United States Patent [19]

Chidsey, III

[11] 4,139,619
[45] Feb. 13, 1979

[54] 6-AMINO-4-(SUBSTITUTED AMINO)-1,2-DIHYDRO-1-HYDROXY-2-IMINOPYRIMIDINE, TOPICAL COMPOSITIONS AND PROCESS FOR HAIR GROWTH

[75] Inventor: Charles A. Chidsey, III, Denver, Colo.

[73] Assignee: The Upjohn Company, Kalmazoo, Mich.

[21] Appl. No.: 826,180

[22] Filed: Aug. 19, 1977

Related U.S. Application Data

[63] Continuation of Ser. No. 689,473, May 24, 1976, abandoned, which is a continuation of Ser. No. 579,559, May 21, 1975, abandoned, which is a continuation of Ser. No. 396,820, Sep. 13, 1973, abandoned, which is a continuation of Ser. No. 213,743, Dec. 29, 1971, abandoned.

[51] Int. Cl.$^2$ .............. A61K 31/535; A61K 31/505; A61L 9/04
[52] U.S. Cl. ................................. 424/45; 424/251; 424/248.56
[58] Field of Search ........................ 424/251, 248

[56] References Cited

U.S. PATENT DOCUMENTS

3,461,461  8/1969  Anthony et al. ................ 424/251

Primary Examiner—Sam Rosen
Attorney, Agent, or Firm—John J. Killinger; Roman Saliwanchik

[57] ABSTRACT

This invention relates to a process for stimulating the growth of mammalian hair comprising the application to mammalian skin of a compound of the formula:

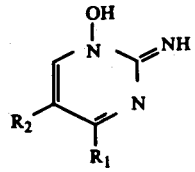

Formula I wherein $R_1$ is a moiety selected from the group consisting of moieties of the formula

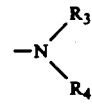

wherein $R_3$ and $R_4$ are selected from the group consisting of hydrogen, lower alkyl, lower alkenyl, lower aralkyl, and lower cycloalkyl, and taken together $R_3$ and $R_4$ may be a heterocyclic moiety selected from the group consisting of aziridinyl, azetidinyl, pyrrolidinyl, piperidino, hexahydroazepinyl, heptamethylenimino, octamethylenimino, morpholino, and 4-lower-alkylpiperazinyl, each of said heterocyclic moieties having attached as substituents on the carbon atoms 0-3 lower alkyl groups, hydroxy or alkoxy wherein $R_2$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloaralkyl and the pharmacologically acceptable acid addition salts thereof in association with a topical pharmaceutical carrier.

9 Claims, No Drawings

6-AMINO-4-(SUBSTITUTED AMINO)-1,2-DIHYDRO-1-HYDROXY-2-IMINOPYRIMIDINE, TOPICAL COMPOSITIONS AND PROCESS FOR HAIR GROWTH

CROSS REFERENCE TO RELATED APPLICATIONS

This application is a continuation of application Ser. No. 689,473, filed May 24, 1976, now abandoned, which is a continuation of application Ser. 579,559, filed May 21, 1975, now abandoned, which in turn is a continuation of application Ser. No. 396,820, filed Sept. 13, 1973, now abandoned, which in turn is a continuation of application Ser. No. 213,743, filed Dec. 29, 1971, now abandoned.

The active compounds of the present invention and method for their preparation are disclosed in U.S. Pat. No. 3,461,461, issued Aug. 12, 1969 and U.S. application Ser. No. 132,153, filed Apr. 7, 1971.

BRIEF DESCRIPTION OF THE INVENTION

This invention relates to pharmaceutical compositions for topical application comprising a compound of the formula I, in the form of the free base or acid addition salts thereof, in association with a pharmaceutical carrier adapted for topical application to mammalian skin.

Another aspect of the invention is a process for increasing the rate of terminal hair growth and a process for stimulating the conversion of vellus hair to growth as terminal hair.

DETAILED DESCRIPTION

Alopecia (baldness) a deficiency of hair, either normal or abnormal, is primarily a cosmetic problem in humans. It is a deficiency of terminal hair, the broad diameter, colored hair that is readily seen. However, in the so-called bald person although there is a noticeble absence of terminal hair the skin does contain vellus hair which is a fine colorless hair which may require microscopic examination to determine its presence. This vellus hair is a precursor to terminal hair. A compound of the formula I can be used to stimulate the conversion of vellus hair to growth as terminal hair as well as increasing the rate of growth of terminal hair.

The present invention finds application in all mammalian species, including both humans and animals. In humans, the compounds of the subject invention can be applied for example, to the head, pubic area, upper lip, eyebrows, and eyelids. In animals raised for their pelts, e.g. mink, the compounds can be applied over the entire surface of the body to improve the overall pelt for commercial reasons. The process can also be used for cosmetic reasons in animals, e.g. applied to the skin of dogs and cats having bald patches due to mange or other diseases.

The pharmaceutical compositions contemplated by this invention include pharmaceutical compositions suited for topical and local action.

The term "topical" as employed herein relates to the use of a compound of the formula I, incorporated in a suitable pharmaceutical carrier, and applied at the site of baldness for exertion of local action. Accordingly, such topical compositions includ those pharmaceutical forms in which the compound is applied externally by direct contact with the skin surface to be treated. Conventional pharmaceutical forms for this purpose include ointments, lotions, pastes, jellies, sprays, aerosols, and the like. The term "ointment" embraces formulations (including creams) having oleaginous, absorption, water-soluble and emulsion-type bases, e.g., petrolatum, lanolin, polyethylene glycols, as well as mixtures of these.

The percentage by weight of the compound of the formula I herein utilized ranges from about 0.1% to about 20.0% of the pharmaceutical preparation, preferably from about 0.5% to about 2% and in these preparations the aforesaid pharmaceutical carrier for topical application constitutes a major amount of the said preparation.

The following examples describe the manner and process of making and using the invention and set forth the best mode contemplated by the inventor of carrying out the invention but are not to be construed as limiting.

EXAMPLE 1 Topical Cream

One-thousand gm. of topical cream is prepared from the following types and amounts of ingredients:

| | |
|---|---|
| 6-amino-1,2-dihydro-1-hydroxy-2-imino-4-piperidinopyrimidine free base | 1 gm. |
| Polysorbate 80 | 50 gm. |
| Tegacid regular* | 150 gm. |
| Spermaceti | 100 gm. |
| Propylene glycol | 50 gm. |
| Methylparaben | 1 gm. |
| Deionized water q.s. | 1000 gm. |

*Self-emulsifying glyceryl monostearate from Goldschmidt Chemical Corporation, New York, N.Y.

The Tegacid and spermaceti are melted together at a temperature of 70-80° C. The methylparaben is dissolved in about 500 gm. of water and the propylene glycol, polysorbate 80, and 6-amino-1,2-dihydro-1-hydroxy-2-imino-4-piperidinopyrimidine free base are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm. and the preparation stirred to maintain homogeneity until cooled and congealed.

The composition is applied to bald human scalp three times a day to stimulate the growth of terminal hair.

EXAMPLE 2 Topical Cream

One-thousand gm. of topical cream is prepared from the following types and amounts of ingredients:

| | |
|---|---|
| 6-amino-1,2-dihydro-1-hydroxy-2-imino-4-piperidinopyrimidine free base | 200 gm. |
| Tegacid regular* | 150 gm. |
| Polysorbate 80 | 50 gm. |
| Spermaceti | 100 gm. |
| Propylene glycol | 50 gm. |
| Methylparaben | 1 gm. |
| Deionized water q.s. | 1000 gm. |

*Self-emulsifying glyceryl monostearate from Goldschmidt Chemical Corporation, New York, N.Y.

The Tegacid and spermaceti are melted together at a temperature of 70-80° C. The methylparaben is dissolved in about 500 gm. of water and the propylene glycol, polysorbate 80, and 6-amino-1,2-dihydro-1- hydroxy-2-imino-4-piperidinopyrimidine free base are added in turn, maintaining a temperature of 75–80° C. The methylparaben mixture is added slowly to the Tegacid and spermaceti melt, with constant stirring. The addition is continued for at least 30 minutes with additional stirring until the temperature has dropped to 40–45° C. Finally, sufficient water is added to bring the final weight to 1000 gm. and the preparation stirred to maintain homogeneity until cooled and congealed.

The composition is applied to bald human scalp once daily to stimulate the growth of terminal hair.

EXAMPLE 3 Topical Ointment

One thousand gm. of a 2% 6-amino-1,2-dihydro-1-hydroxy-2-imino-4-piperidinopyrimidine free base ointment is prepared from the following types and amounts of ingredients:

| | |
|---|---|
| 6-amino-1,2-dihydro-1-hydroxy-2-imino-4-piperidinopyrimidine free base | 20 gm. |
| Zinc oxide | 50 gm. |
| Calamine | 50 gm. |
| Liquid petrolatum (heavy) | 250 gm. |
| Wool fat | 200 gm. |
| White petrolatum q.s. | 1000 gm. |

The white petrolatum and wool fat are melted and 100 gm. of liquid petrolatum added thereto. The 6-amino-1,2-dihydro-1-hydroxy-2-imino-4-piperidinopyrimidine free base, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

The foregoing ointment can be applied topically to mammalian skin for increased rate of terminal hair growth.

The foregoing composition can be prepared by omitting the zinc oxide and calamine.

EXAMPLE 4 Ointment

One-thousand gm. of an ophthalmic ointment containing 10% 6-amino-1,2-dihydro-1-hydroxy-2-imino-4-piperidinopyrimidine free base is prepared from the following types and amounts of ingredients:

| | |
|---|---|
| 6-amino-1,2-dihydro-1-hydroxy-2-imino-4-piperidinopyrimidine free base | 100 gm. |
| Light liquid petrolatum | 250 gm. |
| Wool fat | 200 gm. |
| White petrolatum q.s. | 1000 gm. |

The 6-amino-1,2-dihydro-1-hydroxy-2-imino-4-piperidinopyrimidine free base is finely divided and added to the light liquid petrolatum. The wool fat and white petrolatum are melted together, strained, and the temperature adjusted to 45–50° C. The liquid petrolatum slurry is added and the ointment stirred until congealed. Suitably the ointment is packaged in 30 gm. tubes.

The foregoing ointment can be applied to the eyelid to enhance the growth of eyelashes. Similarly the composition can be applied to the brow for eyebrow growth.

EXAMPLE 5 Solution

One-thousand c.c. of an aqueous solution containing 5% 6-amino-1,2-dihydro-1-hydroxy-2-imino-4-piperidinopyrimidine hydrochloride is prepared from the following types and amounts of ingredients:

| | |
|---|---|
| 6-amino-1,2-dihydro-1-hydroxy-2-imino-4-piperidinopyrimidine hydrochloride | 50 gm. |
| Polyethylene glycol 4000 | 120 gm. |
| Myristyl-γ-picolinium chloride | 0.2 gm. |
| Polyvinylpyrrolidone | 1 gm. |
| Deionized water q.s. ad | 1000 c.c. |

The ingredients are dissolved in the water and the resulting solution is sterilized by filtration. The solution is aseptically filled into sterile cntainers.

The composition so prepared can be used in the topical treatment of baldness by application to the scalp daily.

EXAMPLE 6 Lotion

| | |
|---|---|
| 6-amino-1,2-dihydro-1-hydroxy-2-imino-4 piperidinopyrimidine free base | 1 gm. |
| N-methyl pyrolidone | 40 gm. |
| Propylene glycol q.s. | 1000 gm. |

The 6-amino-1,2-dihydro-1-hydroxy-2-imino-4-piperidinopyrimidine free base is dissolved in the vehicle of N-methyl pyrolidone and propylene glycol.

The composition can be used for application to dogs or cats having hair loss due to mange.

EXAMPLE 7 Aerosol

An aerosol containing approximately 0.01% 6-amino-1,2-dihydro-1-hydroxy-2-imino-4-piperidinopyrimidine free base is prepared from the following types and amounts of materials:

| | |
|---|---|
| 6-amino-1,2-dihydro-1-hydroxy-2-imino-4-piperidinopyrimidine free base | 1.5 gm. |
| Absolute alcohol | 4.37 gm. |
| Dichlorodifluoroethane | 1.43 gm. |
| Dichlorotetrafluoroethane | 5.70 gm. |

The 6-amino-1,2-dihydro-1-hydroxy-2-imino-4-piperidinopyrimidine free base is dissolved in the absolute alcohol and the resulting solution filtered to remove particles and lint. This solution is chilled to about minus 30° C. To this is added the chilled mixture of dichlorodifluoromethane and dichlorotetrafluoroethane. Thirteen ml. plastic-coated amber bottles are cold filled with 11.5 gm. each of the resulting solution and capped.

The composition can be sprayed on the scalp daily to convert vellus hair to growth as terminal hair.

EXAMPLE 8 Dusting Powder

One thousand grams of a powder are prepared from the following types and amounts of ingredients:

| | |
|---|---|
| 6-amino-1,2-dihydro-1-hydroxy-2-imino-4-piperidinopyrimidine | |

-continued

| free base | 10 gm. |
| Bentonite | 100 gm. |
| Talc q.s. | 1000 gm. |

The powdered ingredients are mixed together and dusted on the fur of minks for increased rate of hair growth.

EXAMPLE 9

Following the procedure of the preceding Examples 1 through 8, inclusive, compositions are similarly prepared substituting an equimolar amount of a compound within the scope of fomula 1 disclosed in Examples 1 through 29, inclusive, of U.S. Pat. No. 3,461,461, issued Aug. 12, 1969, for the compound of the example.

I claim:
1. A topical composition for application to mammalian skin comprising an effective amount of a compound of the formula:

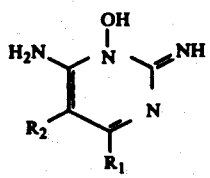

wherein $R_1$ is a moiety selected from the group consisting of moieties of the formula

wherein $R_3$ and $R_4$ are selected from the group consisting of hydrogen, lower alkyl, lower alkenyl, lower aralky, and lower cycloalkyl, and taken together $R_3$ and $R_4$ may be a heterocyclic moiety selected from the group consisting of aziridinyl, azetidinyl, pyrrolidinyl, piperidino, hexahydroazepinyl, heptamethylenimino, octamethylenimino, morpholino, and 4-lower-alkyl-piperazinyl, each of said heterocyclic moieties having attached as substituents on the carbon atoms 0–3 lower alkyl groups, hydroxy or alkoxy, and wherein $R_2$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloaralkyl and the pharmacologically acceptable acid addition salts thereof, in association with a topical pharmaceutical carrier selected from the group consisting of ointments, lotions, pastes, jellies, sprays, and aerosols.

2. The composition of claim 1 wherein the concentration of the compound is from about 0.1% to about 20% of the composition.

3. The composition of claim 1 wherein the compound is 6-amino-1,2-dihydro-1-hydroxy-2-imino-4-piperidinopyrimidine in the form of the free base or acid addition salts thereof.

4. A process for increasing the rate of terminal hair growth in mammalian species comprising the application to mammalian skin at the locale of terminal hair of an effective amount of a compound of the formula:

wherein $R_1$ is a moiety selected from the group consisting of moieties of the formula

wherein $R_3$ and $R_4$ are selected from the group consisting of hydrogen, lower alkyl, lower alkenyl, lower aralkyl, and lower cycloalkyl, and taken together $R_3$ and $R_4$ may be a heterocyclic moiety selected from the group consisting of aziridinyl, azetidinyl, pyrrolidinyl, piperidino, hexahydroazepinyl, heptamethylenimino, octamethylenimino, morpholino, and 4-lower-alkyl-piperazinyl, each of said heterocyclic moieties having attached as substituents on the carbon atoms 0–3 lower alkyl groups, hydroxy or alkoxy, and wherein $R_2$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloaralkyl and the pharmacologically acceptable acid addition salts thereof, in association with a topical pharmaceutical carrier.

5. The process of claim 4 wherein the concentration of the compound applied is from about 0.1% to about 20% of the composition.

6. The process of claim 4 wherein compound applied is 6-amino-1,2-dihydro-1-hydroxy-2-imino-4-piperidinopyrimidine.

7. A process for the conversion of vellus hair to growth as terminal hair comprising the application to mammalian skin at the locale of vellous hair of an effective amount of a compound of the formula:

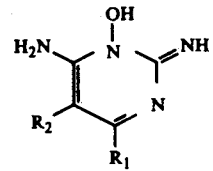

wherein $R_1$ is a moiety selected from the group consisting of moieties of the formula

wherein $R_3$ and $R_4$ are selected from the group consisting of hydrogen, lower alkyl, lower alkenyl, lower aralkyl, and lower cycloalkyl, and taken together $R_3$ and $R_4$ may be a heterocyclic moiety selected from the group consisting of aziridinyl, azetidinyl, pyrrolidinyl, piperidino, hexahydroazepinyl, heptamethylenimino, octamethylenimino, morpholino, and 4-lower-alkylpiperazinyl, each of said heterocyclic moieties having attached as substituents on the carbon atoms 0–3 lower alkyl groups, hydroxy or alkoxy, and wherein $R_2$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloaralkyl and the pharmacologically acceptable acid addition salts thereof, in association with a topical pharmaceutical carrier.

8. The process of claim 7 wherein the concentration of the compound applied is from about 0.1% to about 20% of the composition.

9. The process of claim 7 wherein the compound applied is 6-amino-1,2-dihydro-1-hydroxy-2-imino-4-piperidinopyrimidine.

* * * * *

UNITED STATES PATENT AND TRADEMARK OFFICE
CERTIFICATE OF CORRECTION

PATENT NO. : 4,139,619

DATED : February 13, 1979

INVENTOR(S) : Charles A. Chidsey III

It is certified that error appears in the above-identified patent and that said Letters Patent are hereby corrected as shown below:

Column 1, line 11, "Ser. 579,559" should read --Serial No. 579,559--; line 39, "noticeble" should read --noticeable--; line 50, "applied" should read --applied,--; line 65, "includ" should read --include--. Column 4, line 18, "cntainers" should read --containers--; line 47, "Dichlorodifluoroethane" should read --Dichlorodifluoromethane--. Column 5, line 15, "fomula" should read --formula--; line 41, "aralky," should read --aralkyl,--. Column 6, line 43, "vellous" should read --vellus--.

Signed and Sealed this

Thirtieth Day of October 1979

[SEAL]

Attest:

RUTH C. MASON
*Attesting Officer*

LUTRELLE F. PARKER
*Acting Commissioner of Patents and Trademarks*